(12) United States Patent
Hoyos et al.

(10) Patent No.: US 7,897,044 B2
(45) Date of Patent: Mar. 1, 2011

(54) FLUID SEPARATION DEVICE

(75) Inventors: Mauricio Hoyos, Cretiel (FR); Pascal Kurowski, Paris (FR); Natacha Callens, Verrieres le Buisson (FR)

(73) Assignee: Centre National de la Recherche Scientifique, Paris (FR)

( * ) Notice: Subject to any disclaimer, the term of this patent is extended or adjusted under 35 U.S.C. 154(b) by 842 days.

(21) Appl. No.: 11/851,711

(22) Filed: Sep. 7, 2007

(65) Prior Publication Data

US 2008/0067128 A1    Mar. 20, 2008

Related U.S. Application Data

(63) Continuation of application No. PCT/FR2006/050216, filed on Feb. 13, 2006.

(30) Foreign Application Priority Data

Mar. 11, 2005   (FR)   .................................. 05 50645

(51) Int. Cl.
*B01D 15/08*   (2006.01)
(52) U.S. Cl. ..................... 210/198.2; 210/511; 210/656; 209/18; 209/131; 209/156; 209/422; 422/505
(58) Field of Classification Search ................... 209/18, 209/131, 156, 422; 210/656, 198.2, 511; 422/100, 101
See application file for complete search history.

(56) References Cited

U.S. PATENT DOCUMENTS

| | | | |
|---|---|---|---|
| 6,365,050 B1 * | 4/2002 | Cauchon | 210/635 |
| 6,843,262 B2 * | 1/2005 | Ismagilov et al. | 137/14 |
| 7,373,805 B2 * | 5/2008 | Hawkes et al. | 73/61.71 |
| 2001/0048637 A1 | 12/2001 | Weigl et al. | |
| 2002/0149766 A1 | 10/2002 | Bardell et al. | |
| 2003/0124619 A1 | 7/2003 | Weigl et al. | |

(Continued)

OTHER PUBLICATIONS

Cho, B. S. et al., *Passively Driven Integrated Microfluidic System for Separation of Motile Sperm*, Analytical Chemistry, 75 (2003), pp. 1671-1675.

(Continued)

*Primary Examiner*—Ernest G Therkorn
(74) *Attorney, Agent, or Firm*—Alston & Bird LLP

(57) ABSTRACT

The present invention relates to a fluidic separation device comprising:
 at least one microchannel (2; 66) extending along a longitudinal axis (X), the microchannel having a cross-section that presents a width measured along a first transverse axis (Y) and a thickness measured along a second transverse axis (Z) perpendicular to the first, the width being greater than the thickness, the microchannel including, along the second transverse axis, bottom and top walls (3 and 4);
 at least first, second, and third inlets (7, 8, and 9) in fluidic communication with the microchannel (2), the second inlet (8) being disposed on the second transverse axis (Z) between the first and third inlets (7 and 9); and
 at least first and third transverse separation walls (10 and 11) respectively separating the first and second inlets and the second and third inlets, the first and second separation walls (10; 11) being arranged in such a manner that the second inlet (8) is separated from each of said bottom and top walls (3 and 4) by a non-zero distance measured along the second transverse axis (Z), the second inlet (8) being, in particular, adjacent to at least one of the separation walls.

20 Claims, 5 Drawing Sheets

U.S. PATENT DOCUMENTS

2003/0165812 A1 9/2003 Takayama et al.
2003/0234210 A1 12/2003 Deshpande et al.
2009/0292234 A1* 11/2009 Leonard et al. ............ 604/5.04

OTHER PUBLICATIONS

Fisher, D. et al., *Cell Separation, A Practical Approach*, Eds. Oxford, PAS 193 (1998); 24 sheets.

Fu, A. Y. et al., *A Microfabricated Fluorescence-Activated Cell Sorter*, Nature Biotechnology, vol. 17, Nov. 1999, pp. 1109-1111.

MacDonald, M. et al., *Microfluidic Sorting in an Optical Lattice*, Nature 426 (2003), pp. 421-424.

McClain, M. A. et al., *Microfluidic Device for High Throughput Chemical Analysis of Cells*, Analytical Chemistry, 75 (2003), pp. 5646-5655.

Recktenwald, D. et al., *Cell Separation Methods and Applications*, Eds. Marcel Dekker(1997); Book Cover and pp. 153-235.

Saldanha, A. D. et al., *Viral Separations Using a Microfabricated Electrical SPLITT System*, Proc. of Micro-TAS 2002, Nara, Japan 2002.

Voldman, J. et al., *A Microfabrication-Based Dynamic Array Cytometer*, Analytical Chemistry, 74(2002), pp. 3984-3990.

Weigl, B. H. et al., *Lab-on-a-chip-based Separation and Detection Technology for Life Science Applications*, American Biotechnology Laboratory, Jan. 2002, pp. 28-30.

Weigl, B. H. et al., *Microfluidic Diffusion-Based Separation and Detection*, Science, vol. 283 (1999), pp. 346-347.

Wheeler, A. R. et al., *Microfluidic Device for Single-Cell Analysis*, Analytical Chemistry, 75 (2003), pp. 3581-3586.

Wolff, A. et al., *Integrating Advanced Functionality in a Microfabricated High-Throughput Fluorescent-Activated Cell Sorter*, Lab-on-a-ship, 3, (2003), pp. 22-27.

\* cited by examiner

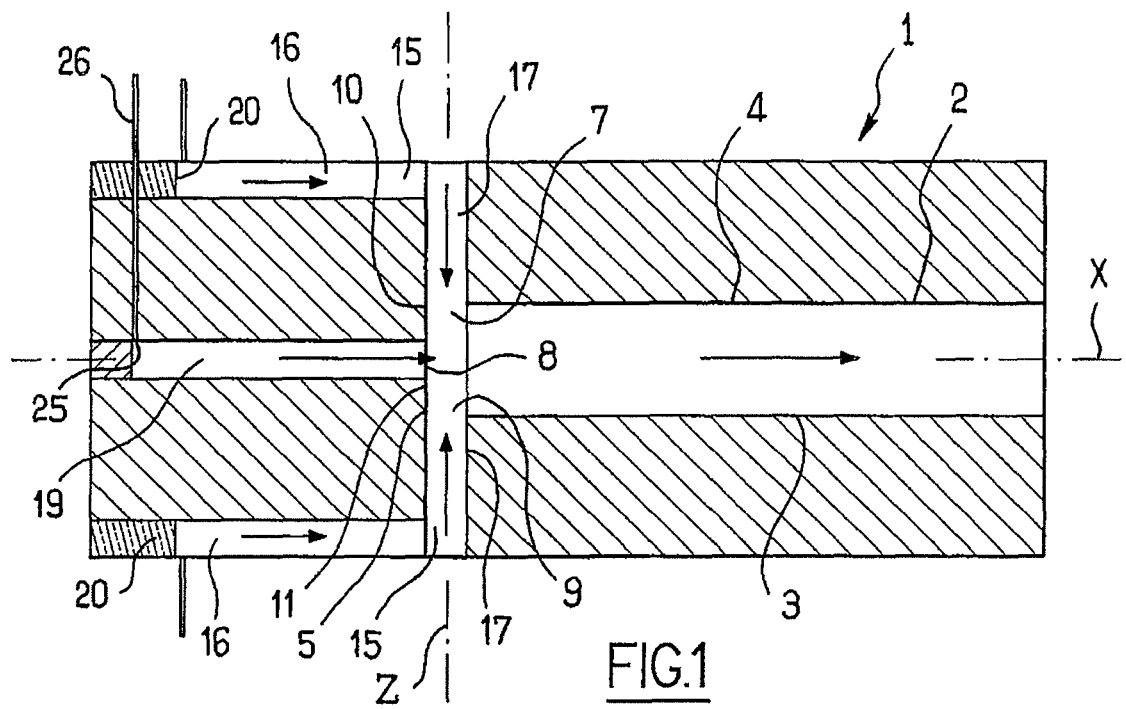
FIG.1
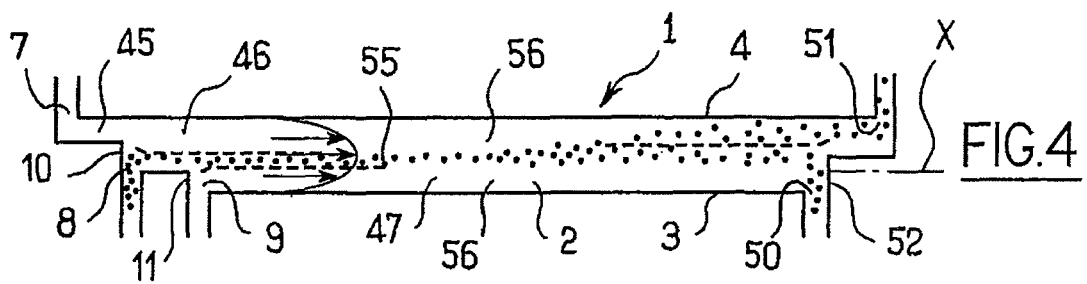
FIG.4
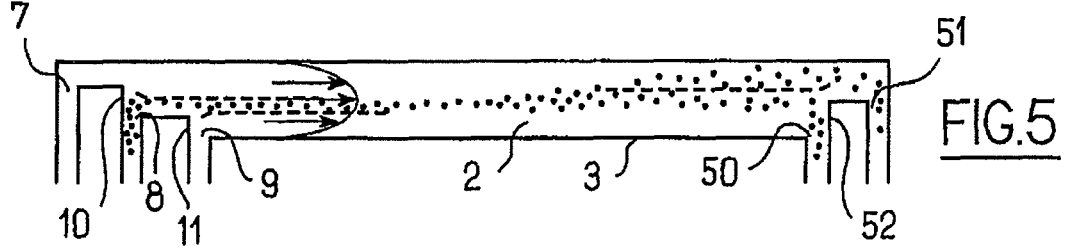
FIG.5
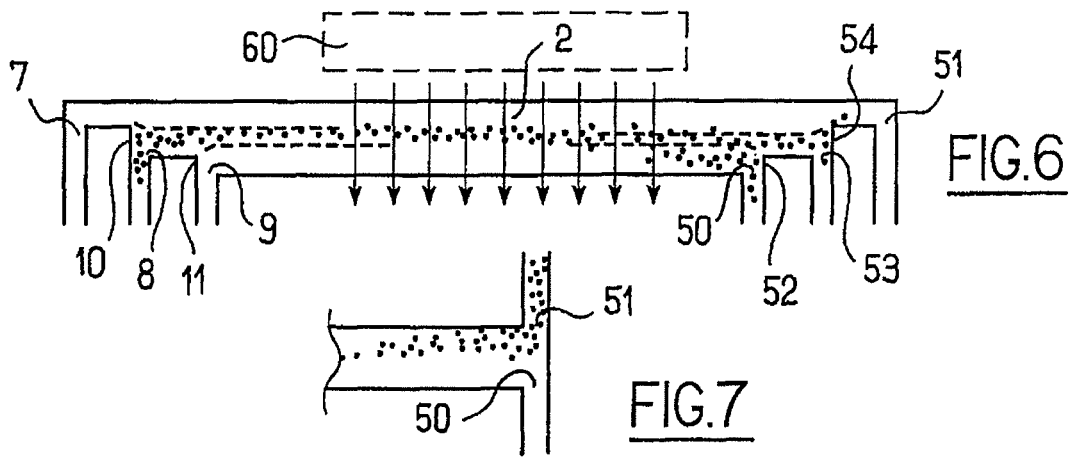
FIG.6
FIG.7

FLUID SEPARATION DEVICE

REFERENCE TO RELATED APPLICATIONS

This application is a continuation of PCT/FR06/50216 filed Feb. 13, 2006.

The invention relates to a fluidic separation device, in particular a microfluidic device, and to applications thereof.

In conventional manner, cells are sorted by means of membranes or filters or by methods of elutriation, or of centrifuging with Ficol®, Percoll®, or other stationary phases. Nevertheless, for certain applications, such as for example separating cells that are infected with parasites, existing separation devices can be found to be insufficiently effective.

Separation methods are also known that make use of magnetic or electric fields, as described in the works *Cell separation methods and applications*, by D. Recktenwald, A. Radbruch, Eds. Marcel Dekker 1997, and *Cell separation, a practical approach*, by D. Fisher, G. E. Francis, Eds. Oxford, PAS 193, 1998. Those methods may optionally use stationary phases.

Methods using a magnetic field require prior processing of the samples since the cells do not present sufficient natural magnetization to enable them to be separated.

Flow cytometry is in widespread use for the purposes of sorting and characterizing blood cells. That method enables a plurality of species to be sorted simultaneously with high selectivity. Nevertheless, flow cytometry is not suitable for performing preparative or semi-preparative separations, since separation is then performed cell by cell, and even at a rate of about 15,000 cells per second, that method cannot be considered as constituting a preparative method.

Microfluidic devices for performing separation are also described in the following articles:

*Integrating advanced functionality in a microfabricated high-throughput fluorescent-activated cell sorter*, A. Wolff, I. Peter-Nielsen, U. Larsen, P. Friis, G. Goranovic, C. Poulsen, J. Kutter, P. Telleman, *Lab-on-a-ship*, 3, 2003, 22-27,

*Lab-on-a-chip-based separation and detection technology for life science applications*, B. H. Weigl and K. Hedine, *American Biotechnology Laboratory*, January 2002, 28-30,

*A microfabricated fluorescence-activated cell sorter*, A. Y. Fu, Ch. Spenser, A. Scherer, F. Arnold and S. Quake, *Nature Biotechnology*, vol. 17, November 1999, 1109-1111.

*A microfabrication-based dynamic array cytometer*, J. Voldman, M. L. Gray, M. Toner and M. A. Schmidt, *Analytical Chemistry*, 74, 2002, 3984-3990,

*Microfluidic device for single-cell analysis*, A. R. Wheeler, W. R. Throndset, R. J. Whelan, A. M. Leach, R. N. Zare, Y. H. Liao, K. Farrell, I. D. Manger and A. Daridon, *Analytical Chemistry*, 75, 2003, 3581-3586,

*Microfluidic device for high throughput chemical analysis of cells*, M. A. McClain, C. T. Culbertson, S. C. Jacobson, N. L. Allbritton, C. E. Sims and M. Ramsey, *Analytical Chemistry*, 75, 2003, 5646-5655,

*Passively driven integrated microfluidic system for separation of motile sperm*, B. S. Cho, T. G. Schuster, X. Zhu, D. Chang, G. D. Smith and S. Takayama, *Analytical Chemistry*, 75, 2003, 1671-1675,

*Microfluidic optical sorting*, M. MacDonald, G. Spalding and K. Dholakaia, *Nature* 426, 2003, 421-424,

*Microfluidic diffusion-based separation and detection*, B. H. Weigl and P. Yager, *Science*, vol. 283 1999, 346-347.

Those devices are inexpensive and use little reagent and material for analysis.

Another advantage is the possibility of combining a large number of units in a small area or volume, thus making it possible to process a large quantity of material even if each unit makes use of little. In addition, microfluidic devices are particularly advantageous for biological applications since they can be discardable, for single use only, which in medicine serves to avoid problems of contamination.

US patent application US 2003/0234210 discloses a separation device for separating particles in suspension and comprising a plurality of outlet channels. That device is also provided with valves capable of generating pressure pulses for controlling flow in the channels.

US patent application US 2003/0165812 discloses a sorting device, e.g. for sorting spermatozoa, that device having two inlet channels and two outlet channels making an angle of about 45° relative to each other.

US patent application 2003/0124619 describes a separation device having an H-filter configuration, that device being used for separating macromolecules having different diffusion coefficients.

US patent application US 2002/0149766 describes a microcytometer.

US patent application 2001/0048637 discloses a microfluidic device having two inlet channels that are connected perpendicularly to a central channel.

Split-flow lateral-transport thin separation cell (SPLITT) type separation devices are also known that comprise flow dividers each formed, for example, by a rigid or semirigid blade, as described in the article *Viral separations using a microfabricated electrical SPLITT system*, by A. D. Saldanha, B. Gale, in Proc. of Micro-TAS 2002, Nara, Japan, 2002. Those flow dividers make it possible to prevent the appearance of points of stagnation or zones of recirculation in the flow with species being trapped at the inlets and at the outlets.

In some devices, separation is performed across the width of the microchannel, thereby tending to limit the number of particles that can be separated simultaneously.

For SPLITT separation devices that can separate species across the thickness of a microchannel, flow rate dividers can optionally be used. When such flow dividers are small in size, they are difficult to implement.

When flow dividers present excessive thickness, they can disturb the flow downstream (recirculation zones being created and particles being trapped, for example). Flow dividers must thus be made to be small in thickness, in which case they are of small stiffness and can deform as a result of a pressure difference on either side thereof.

In separation devices using flow dividers, it is difficult to have more than two inlets or outlets.

Below, the term "microfluidic device" is used to designate a device making use of the transport of a substance within at least one microchannel. The term "microchannel" is used to designate a channel that has a section, over at least a fraction of its length, with at least one dimension measured in a straight line from one side to an opposite side that is less than 1 millimeter.

By way of example, a microchannel may present a width of 4 centimeters (cm), a length of 20 cm, and a thickness of 100 micrometers (µm).

The present invention seeks in particular to improve devices for sorting and/or separating species.

In one of its aspects, the invention provides a fluidic separation device, in particular a microfluidic device, comprising:

at least one microchannel extending along a longitudinal axis, the microchannel having a cross-section that presents a width measured along a first transverse axis and a thickness measured along a second transverse axis perpendicular to the first, the width being greater than the thickness, the microchannel including, along the second transverse axis, bottom and top walls; and at least first, second, and third inlets in fluidic communication with the microchannel, the second inlet being disposed on the second transverse axis between the first and third inlets.

In an embodiment of the invention, the device further comprises at least first and second transverse separation walls respectively separating the first and second inlets and the second and third inlets, the first and second separation walls being arranged in such a manner that the second inlet is separated from each of said bottom and top walls by a non-zero distance measured along the second transverse axis, the second inlet being, in particular, adjacent to at least one of the separation walls.

The device of the invention enables a substance containing species to be caused to circulate, with hydrodynamic focusing, through the second inlet and along the microchannel in such a manner as to form a sheet of substance that is spaced apart from the bottom and top walls of the microchannel, thus making it possible to reduce the effects of interaction between the substance and said walls, in particular the effects due to hydrodynamic buoyancy forces, to lubrication, to electrostatic interactions, to Van Der Waals forces, and to hydrodynamic diffusion effects induced by shear.

The sheet of substance as formed in this way can be stable, with flow lines that are substantially parallel to the longitudinal axis of the microchannel.

By means of the invention, it is possible to have a sheet of relatively small thickness by making the separation walls of appropriate height.

The device makes it possible to sort and/or separate over the thickness of the microchannel.

By providing the device of the invention with a predetermined number of inlets and of separation walls, e.g. more than three inlets, it is possible within the device to perform operations such as mixing species.

The device of the invention need not have a flow divider.

By way of example, the microchannel may present a width/thickness ratio that is greater than or equal to 2, e.g. greater than or equal to 5 or 10.

The invention makes it possible to have a flow along the microchannel with a speed profile that can be considered as being two-dimensional, e.g. over at least 90% of the width of the microchannel, providing the width/thickness ratio is greater than or equal to 10.

Furthermore, because the width of the microchannel can be relatively large compared with its thickness, the quantity of substance flowing in the microchannel can be relatively high, even if the thickness of the microchannel is relatively small.

The cross-section of the microchannel may be constant or otherwise.

The thickness of the microchannel may be constant or varying, e.g. having at least two zones presenting different thicknesses that follow one another axially.

The cross-section may be rectangular for example, or it may be in the form of a dish.

The thickness of the microchannel may lie in the range about 20 µm to about 1000 µm, e.g. in the range 20 µm to 500 µm or 20 µm to 50 µm, being of width lying in the range about 0.5 millimeters (mm) to 10 cm, e.g. in the range 0.5 mm to 5 mm, and of length measured along the longitudinal axis lying in the range about 1 cm to 10 cm, or greater than 10 cm.

The separation walls may optionally be identical in height, as measured along the second transverse axis.

Preferably, at least one of said three inlets presents a width that is not less than the width of the microchannel and/or presents a section that is substantially rectangular.

In an embodiment of the invention, at least one of the three inlets opens out in one of the bottom and top walls of the microchannel and another one of the three inlets opens out in the other one of the bottom and top walls of the microchannel.

By way of example, the first and third inlets are disposed facing each other.

In a variant, all three inlets open out either into the bottom wall or into the top wall of the microchannel.

In an embodiment of the invention, the first and third inlets are offset relative to each other along the longitudinal axis of the microchannel.

The second inlet may open out into the microchannel substantially parallel to or perpendicular to the longitudinal axis thereof.

The second inlet may advantageously be adjacent to or upstream from at least one of the separation walls.

In an embodiment of the invention, the device includes at least one feed orifice associated with one of said three inlets, the feed orifice being in fluidic communication with said inlet via a duct, the duct including in particular a diverging portion that diverges from a tip of the duct, the feed orifice opening out into the duct adjacent to said tip, and in particular perpendicularly to the duct.

This diverging portion of the duct makes it possible to form a sheet of substance starting from a feed point.

In an embodiment of the invention, the device includes at least first and second outlets in fluidic communication with the microchannel, and separated from each other by a transverse separation wall of non-zero height measured along the second transverse axis.

The first and second outlets serve to recover species that have migrated within the microchannel, e.g. as a function of their sizes, their diffusion coefficients, or the intensities of the interaction of the species with the force field applied to the microchannel.

The invention makes it possible to perform separation continuously without using filter membranes or dialysis.

The first and second outlets may be offset relative to each other along the longitudinal axis of the microchannel. In a variant, the first and second outlets may be disposed facing each other.

In an embodiment of the invention, the device further comprises a third outlet, the second outlet being disposed between the first and third outlets along the second transverse axis, the first and second outlets and the second and third outlets being mutually separated by respective transverse separation walls of non-zero height measured along the second transverse axis.

Species may be recovered at the outlets without significant disturbance.

In an embodiment of the invention, the device includes at least one outlet orifice associated with one of said outlets of the microchannel, said orifice being in fluidic communication with said outlets via a duct, the duct includes a portion of section that narrows laterally, in particular a portion converging towards a tip, said portion being triangular in shape when observed from above, for example, the outlet orifice opening out into the duct, e.g. adjacent to the tip, and in particular perpendicularly to the duct.

This converging portion of the duct serves to avoid a stagnation point forming at the outlet orifice.

In an embodiment of the invention, the device is arranged to generate at least one transverse force field within at least a fraction of the microchannel, in particular a gravitational, electric, magnetic, or acoustic field, so as to cause the species to migrate in the direction of the second transverse axis, for example.

By means of the invention, the transverse force field may be applied in relatively easy manner since the force field can be applied over the width of the microchannel, which width can be relatively large, instead of being applied across its thickness.

In an embodiment of the invention, the device includes at least one sheet, in particular a stack of at least two sheets, e.g. of plastics material or of metal, forming the microchannel, at least in part.

The sheet or stack of sheets may be sandwiched between at least two plates, in particular of plastics material, e.g. of Plexiglass®.

In general, the microchannel may be made out of various types of material, in particular out of plastics material, e.g. out of polydimethylsiloxane (PDSM), or out of glass.

The microchannel may be fabricated using conventional fabrication methods of the kind used in the field of microfluidics.

Where appropriate, the device may include an array of microchannels, in particular disposed in parallel, and making it possible when so desired to process a large volume of substance, with species being recovered separately for each microchannel, or in a variant with the help of one or more outlets that are common to a plurality of microchannels.

Where appropriate, the microchannel may be provided with at least one valve, e.g. a solenoid valve.

In another of its aspects, the invention also provides the use of the device as specified above, in one of the following applications: methods of sorting species, in particular macromolecules, e.g. rigid or deformable particles, biological cells, in particular blood cells, e.g. cancer cells in a blood sample, bacteria, colloidal or non-colloidal emulsions, proteins, liposomes, emulsions, diagnosis or analysis methods, purification methods, methods of enriching or depleting species, methods of synthesizing species, methods of modifying physical or chemical characteristics of species, methods of searching for medicaments, methods of mixing, methods of measuring diffusion coefficients.

By way of example, the device may be used for enriching a fluid sample with specific cells or platelets, e.g. cancer cells, lymphocytes, or stem cells. The sample as enriched in this way can then be analyzed or processed, e.g. for diagnosis and/or for forming new species and/or for isolation.

By reducing the effects due to interaction with the walls of the microchannel, the invention makes it possible to avoid damaging certain types of biological structure, in particular platelets which are particularly sensitive to shear.

The device may also be used to enrich species with macrophages infected by parasites for performing electro-physiological studies.

The device of the invention makes it possible to perform preparative separations when the device operates continuously and enables tens of millions of particles or cells to be processed per second, where appropriate.

In another of its aspects, the invention also provides a method, in particular a method of sorting and/or separating species contained in a substance, the method being characterized by the fact that it comprises the following steps:

causing a substance containing species to circulate, preferably in continuous manner, within a device as specified above, along its microchannel via said second inlet; and causing one or more carrier fluids to flow, preferably in continuous manner, along the microchannel via said first and second inlets in such a manner that the substance containing the species flows along at least a fraction of the microchannel in the form of a sheet that is spaced apart from the bottom and top walls of the microchannel.

The method may include the following step:

placing the microchannel in at least one transverse force field, at least while a flow is established in the microchannel, the force field being in particular a gravitational, electric, magnetic, or acoustic field, the field being optionally permanent, variable, or constant, depending on the operations to be performed.

The method may include the following step:

causing the species to migrate under the effect of hydrodynamic buoyancy forces or under the effect of hydrodynamic diffusion induced by shear.

The method may also include the following step:

recovering the species that have migrated from at least one of said outlets of the microchannel.

By way of example, the species may be blood platelets or other human, animal, or plant cells.

In another of its aspects, the invention also provides a fluidic separation device, in particular a microfluidic device, comprising:

at least one microchannel extending along a longitudinal axis, the microchannel having a cross-section presenting a width measured along a first transverse axis and a thickness measured along a second transverse axis perpendicular to the first, the width being greater than the thickness, the microchannel including along the second transverse axis, bottom and top walls;

at least first and second inlets in fluidic communication with the microchannel; and at least one transverse separation wall separating the first and second inlets, said separation wall being arranged in such a manner that the second inlet is separated from one of said bottom and top walls by a non-zero distance measured along the second transverse axis, the second inlet being in particular adjacent to the separation wall;

the device including at least one sheet having a cutout forming at least part of a flow channel, said sheet being sandwiched between at least two plates.

At least one of the two plates may be substantially rigid and the sheet may be substantially floppy or flexible.

By way of example, the thickness of a plate is greater than that of a sheet.

The device may be deformable at least in part so as to make it possible, by deformation, to provide the microchannel with a shape that is not rectilinear.

By way of example, the microchannel may be formed with sheets and/or plates made of deformable material.

The outside shape of the device may be substantially cylindrical.

In a variant, the microchannel may be made by machining, in particular by machining in a plate.

In another of its aspects, the invention also provides a method of fabricating a fluidic separation device, in particular a microfluidic device, comprising:

at least one microchannel extending along a longitudinal axis, the microchannel having a cross-section presenting a width measured along a first transverse axis and a thickness measured along a second transverse axis perpendicular to the first, the width being greater than the thickness, the microchannel including along the second transverse axis, bottom and top walls;

at least first and second inlets in fluidic communication with the microchannel; and at least one transverse separation wall separating the first and second inlets, said separation wall being arranged in such a manner that the second inlet is separated from one of said bottom and top walls by a non-zero distance measured along the second transverse axis, the second inlet being in particular adjacent to the separation wall;

the method comprising the following step:

placing a sheet having a cutout forming at least part of the flow channel between at least two plates.

BRIEF DESCRIPTION OF DRAWINGS

The present invention can be better understood on reading the following detailed description of non-limiting embodiments of the invention, and on examining the accompanying drawings, in which:

FIG. 1 is a diagrammatic and fragmentary cross-section view of a device in accordance with the invention;

FIGS. 4 to 7 are diagrammatic and fragmentary views of devices constituting other embodiments of the invention;

DESCRIPTION OF THE PREFERRED EMBODIMENTS

FIG. 1 shows a device 1 in accordance with the invention, comprising a microchannel 2 extending along a longitudinal axis X.

Figure 3:
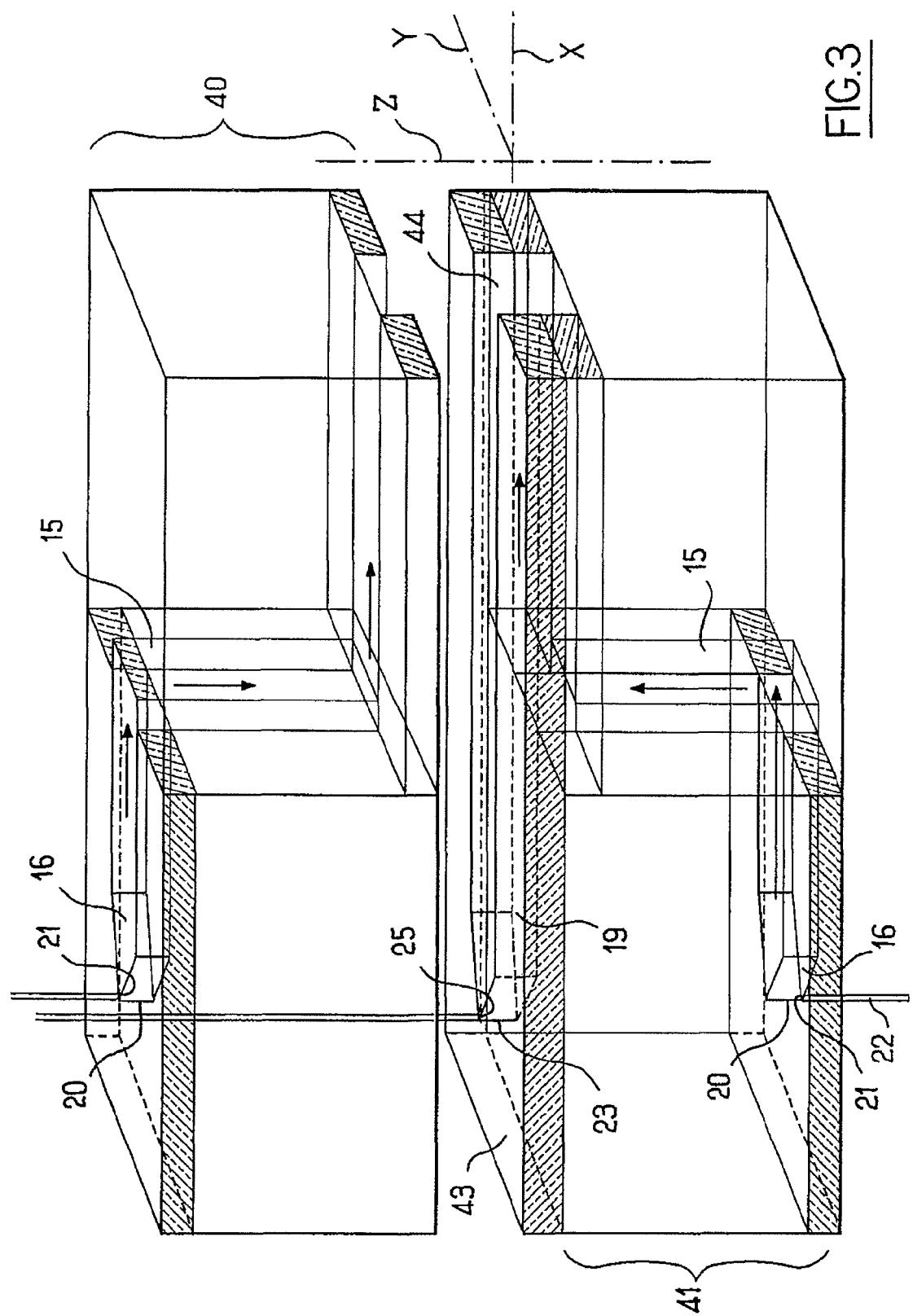

The microchannel 2 presents a cross-section that is rectangular, of width measured along a first transverse axis Y, and of thickness measured along a second transverse axis Z, as shown in FIG. 3.

In the example described, the length/thickness ratio of the microchannel is greater than 10.

The width of the microchannel may be about 0.5 cm, its thickness about 440 μm, and its length about 12 cm.

The microchannel 2 has bottom and top walls 3 and 4 perpendicular to the axis Z.

The microchannel 2 has first, second, and third inlets 7, 8, and 9 at an axial end 5.

The first and third inlets 7 and 9 open out respectively in the top and bottom walls 4 and 3 of the microchannel 2, perpendicularly to the X axis, and facing each other.

The second inlet 8 opens out into the microchannel 2 parallel to the X axis.

The inlets 7 to 9 are of substantially rectangular section, and of width equal to the width of the microchannel 2.

The first inlet 7 and the second inlet 8, are separated by a first transverse separation wall 10, and the second inlet 8 and the third inlet 9 are separated by a second transverse separation wall 11, these separation walls 10 and 11 being perpendicular to the longitudinal axis X.

As can be seen in FIG. 1, the separation walls 10 and 11 are both adjacent to the second inlet 8 and are adjacent respectively to the first and third inlets 7 and 9.

The first and third inlets 7 and 9 are each fed via a duct 15 having a first portion 16 parallel to the X axis and a second portion 17 parallel to the Z axis.

The second inlet 8 is fed by a duct 19 parallel to the X axis.

The first portions 16 of the ducts 15 diverge in shape from respective tips 20, and are in particular triangular in shape when seen from above along the Z axis, with respective orifices 21 adjacent to the tips 20 opening out into the portions 16 perpendicularly thereto, as can be seen in FIG. 3.

Each feed orifice 21 can be connected to a supply of substance (not shown), e.g. via a duct 22.

The duct 19 presents a shape that diverges from a tip 23, in particular a triangular tip, as shown in FIG. 3.

A feed orifice 25 adjacent to the tip 23 opens out into the duct 19, perpendicularly thereto.

The feed orifice 25 may be connected to a supply of substance (not shown) via a duct 26.

The ducts 22 and 26 may present a cross-section that is circular, for example.

The shape of the portions 16 and of the duct 19 make it possible, from an injection point, to form a flow in the form of a sheet presenting width equal to the width of the microchannel 2.

The second inlet 8 presents thickness that is smaller than that of the microchannel 2, e.g. less than half its thickness.

As can be seen, by increasing the height of the separation walls 10 and 11 along the transverse Z axis, it is possible to decrease the thickness of the second inlet 8 in such a manner as to reduce the thickness of the sheet of substance coming from said inlet 8.

If so desired, the thickness of the sheet may also be controlled by manipulating the flow rates coming from the inlets 7 and 9.

It is also possible, in particular by selecting the heights for the separation walls 10 and 11, to position the sheet coming from the inlet 8 at a height that is selected in the thickness direction of the microchannel.

The device 1 may be of the single-use type, and, where appropriate, it need not have any active systems.

There follows a description of the steps in fabricating the microfluidic device 1.

Figure 2:
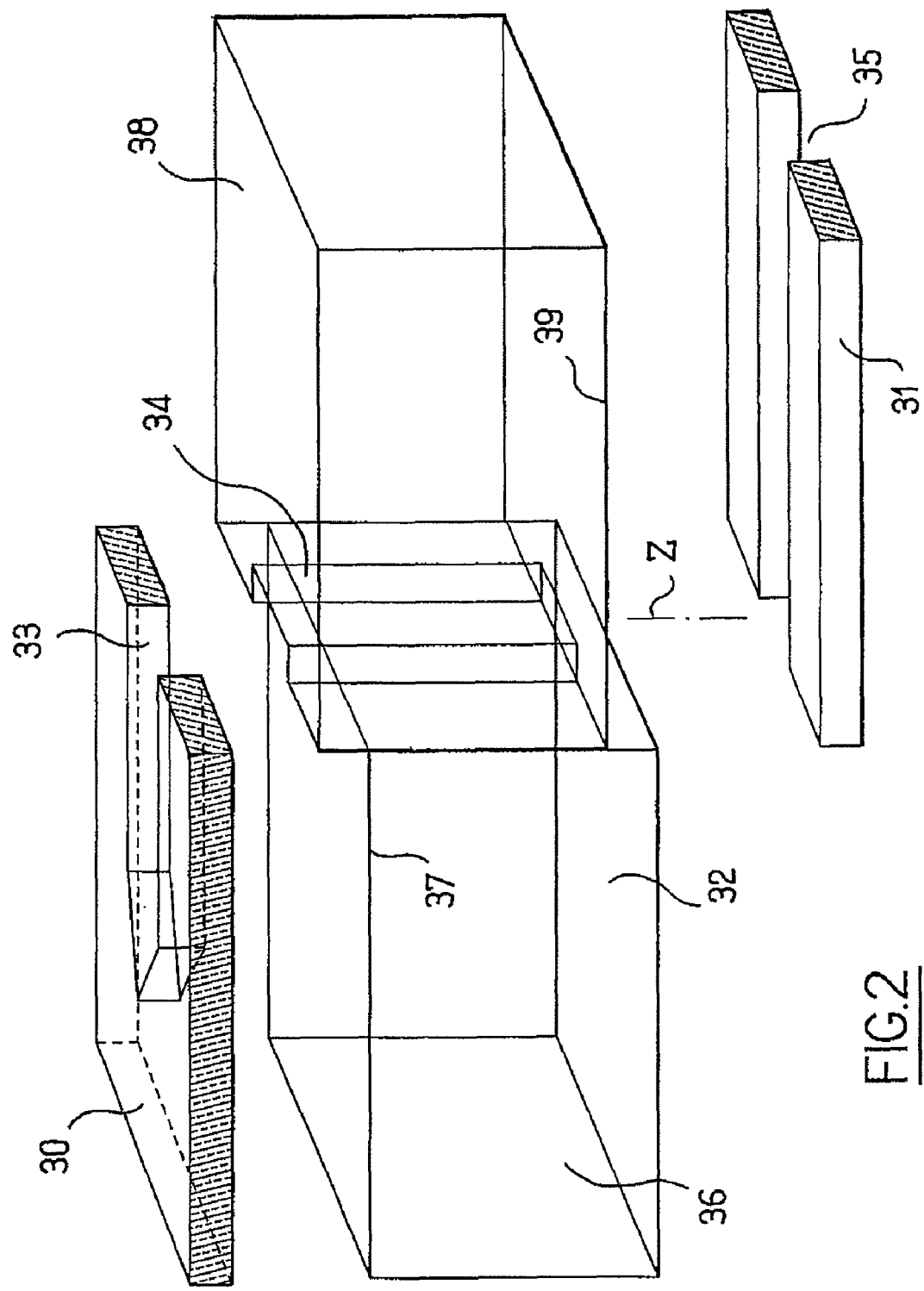
FIGS. 2 and 3 are diagrammatic and fragmentary perspective views showing two steps in fabricating the FIG. 1 device.

As shown in FIG. 2, sheets 30 and 31 are assembled with a plate 32.

The sheet 30 has a cutout 33 for forming the portion 16 of the duct 15.

The plate 32 includes a passage 34 on the Z axis for forming the portion 17 of the duct 15.

The sheet 31 includes a cutout 35 for forming a portion of the microchannel 2.

In the example described, the sheets 30 and 31 are made of plastics material, e.g. of Mylar®.

In a variant, one of the sheets 30 and 31 may be of polyimide.

In a variant, the sheets 30 and 31 may be made of metal, for example.

The plate 32 may be made of plastics material, e.g. of Plexiglass®, or of polycarbonate, as a single piece or as an assembly of a plurality of portions.

The plate 32 has a first portion 36 with a top face 37 for receiving the sheet 30.

The plate 32 has a second portion 38 presenting the same height along the Z axis as the first portion 36 and offset relative thereto through a distance equal to the distance of each of the sheets 30 and 31.

The sheet 30 is fastened on the top face 37 of the first portion 36, and the sheet 31 is fastened on the bottom face 39 of the second portion 38 so as to form a first assembly 40, as shown in FIG. 3.

The sheets 30 and 31 may be fastened on the plate 32 by means of an adhesive, for example.

A second assembly 41 symmetrical to the assembly 40 about the plane defined by the axes X and Y is also fabricated.

A sheet 43 is interposed between the assemblies 40 and 41, the sheet 43 presenting a cutout 44 for forming firstly the duct 19 and secondly, together with the cutouts 35 in the assemblies 40 and 41, the microchannel 2.

Outlets from the microchannels 2 can be made in analogous manner.

In the embodiment described above, the first and third inlets 7 and 9 open out facing each other.

In a variant, as shown in FIG. 4, the first and third inlets 7 and 9 may be offset along the X axis.

In the example in question, the separation walls 10 and 11 are also offset along the X axis.

The first inlet 7 opens out into a first zone 45 presenting thickness along the Z axis, this first zone being connected to a second zone 46 of greater thickness into which the second inlet 8 opens out.

The second zone 46 is connected to a central zone 47 of the microchannel 2.

The differences in thickness between the zones 45 and 46, and between the zones 46 and 47, correspond to the height of the separation wall 10 and to the height of the separation wall 11, respectively.

This offset disposition of the inlets 7 to 9 along the X axis, makes it possible to provide the microchannel 2 with a number of inlets that is greater than three, e.g. four or five.

The microchannel 2 has two outlets 50 and 51 that are offset along the X axis and that are separated from each other by a transverse separation wall 52 perpendicular to the X axis.

In the example shown in FIG. 4, the inlet 7 opens out into the top wall 4 of the microchannel and the inlets 3 and 4 into the bottom wall 3 of the microchannel.

In a variant, as shown in FIG. 5, the inlets 7 to 9 all open out into the bottom wall 3 of the microchannel.

The outlets 50 and 51 can open out one into the bottom wall 3 of the microchannel and the other into the top wall 4, as shown in FIG. 4, or in a variant, they can both open out into one or other of the bottom and top walls 3 and 4, as shown in FIG. 5.

The microchannel 2 may have a number of outlets that is greater than 2.

For example, and as shown in FIG. 6, the microchannel 2 may have three outlets 50, 51, and 53, that are offset along the X axis and that are separated in pairs by transverse separation walls 52 and 54.

Where appropriate, the outlets 50 and 51 may open out facing each other, as shown in FIG. 7.

The device 1 can be used as follows.

As shown in FIG. 4 for example, a carrier fluid 56 is caused to flow via the first and their inlets 7 and 9, while a substance 55 containing species to be sorted and/or separated is caused to travel via the second inlet 8.

When the flow within the microchannel 2 is steady, the sheet of substance 55 between the carrier fluid 56 is kept away from the bottom and top walls 3 and 4 of the microchannel 2 over at least a certain fraction of its length, so as to reduce interactions between the substance 55 and the walls 3 and 4.

Within at least a portion of the microchannel 2, it is possible to generate a transverse force field, for example with the help of a device 60 as shown in FIG. 6.

This transverse force field may be an electric field, a magnetic field, or an acoustic field.

The species contained in the sheet of substance 55 can migrate transversely under the effect of a transverse force field, e.g. a gravitational field, or under the action of hydrodynamic effects, such as for example buoyancy forces or diffusion forces induced by shear.

The effect due to hydrodynamic buoyancy depends on the size of the species.

The hydrodynamic diffusion induced by shear depends on the local shear, on the sizes, and on the concentrations of the species.

The transverse force field may be applied over the entire length of the microchannel 2, or over a fraction only thereof.

The species that have migrated are recovered via one or the other outlets 50 or 51.

The species are separated at the outlets 50 and 51 as a function of their sizes or of their particle diffusion coefficients, or of the intensity of the transverse force field that is applied, if any.

The device 1 can be used as an analytic separator in the field of diagnostic methods, e.g. in order to determine different types of cell in a heterogeneous sample.

Where appropriate, the device 1 may have one or more valves for controlling the injection of substance via the inlets 7 to 9, where such a valve may, for example, be a solenoid valve presenting a single passage or multiple passages.

The injection of substance via the inlets 7 to 9 can be controlled in frequency and in flow rate so as to enable the device 1 to operate continuously in order to process large volumes of substance.

The device 1 of the invention makes it possible to separate particles, macromolecules, colloids, biological cells, e.g. blood cells, cancer cells, or bacteria.

Figure 8:
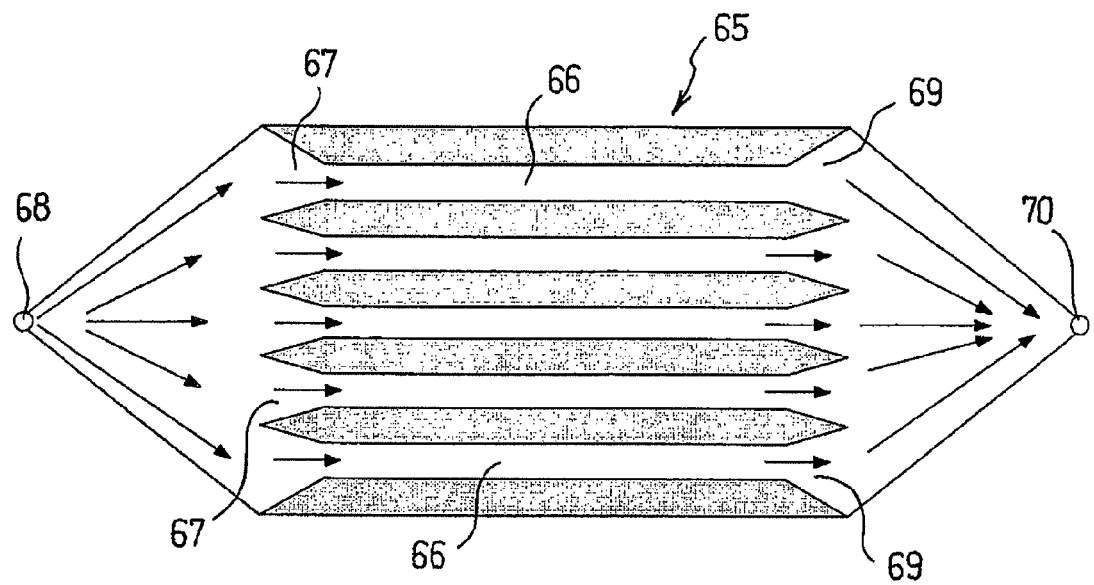
FIGS. 8 and 9 are diagrammatic and fragmentary views of devices in accordance with the invention, each having an array of microchannels.

FIG. 8 is a plan view looking along the Z axis showing a microfluidic device 65 in accordance with the invention that has an array of microchannels 66 disposed in parallel.

In the example described, the device 65 has a plurality of feed orifices 68 like the above-described feed orifices 21 and 25.

The inlets 67 of the microchannels 66 are of converging shape so as to direct the flow into the microchannel 66 in question.

The outlets 69 are of diverging shape and they are connected to outlet orifices 70.

The device 65 enables a larger volume of substance to be processed.

The species that have migrated can be recovered individually for each microchannel 66, or in a variant, via outlets that are common to a plurality of microchannels 66.

Figure 9:
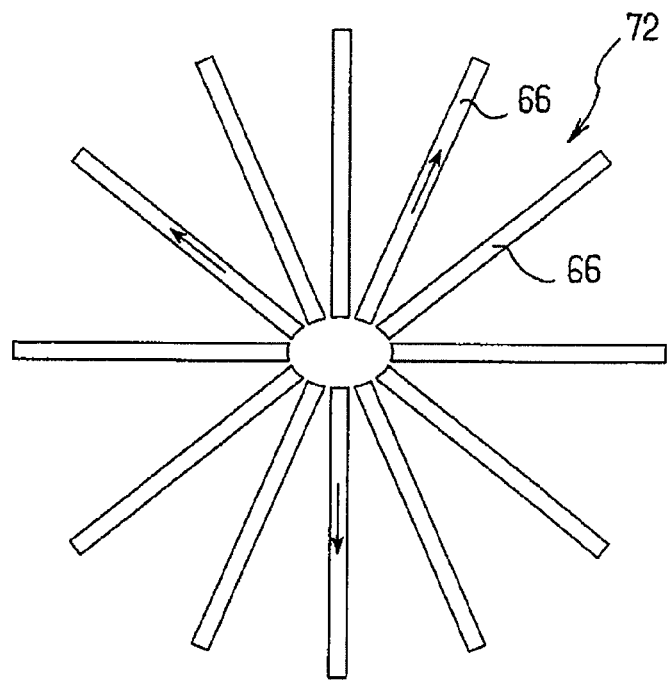

FIG. 9 shows a microfluidic device 72 having microchannels 66 disposed in a star configuration, e.g. connected to a common inlet.

Each microchannel 66 may have its own outlets.

Naturally, the invention is not limited to the embodiments described above.

For example, the microchannel 2 could have a number of inlets greater than 3.

In a variant, the microchannel 2 could comprise, for example, a single inlet together with at least three outlets, or at least three inlets together with a single outlet.

Figures 10, 11:
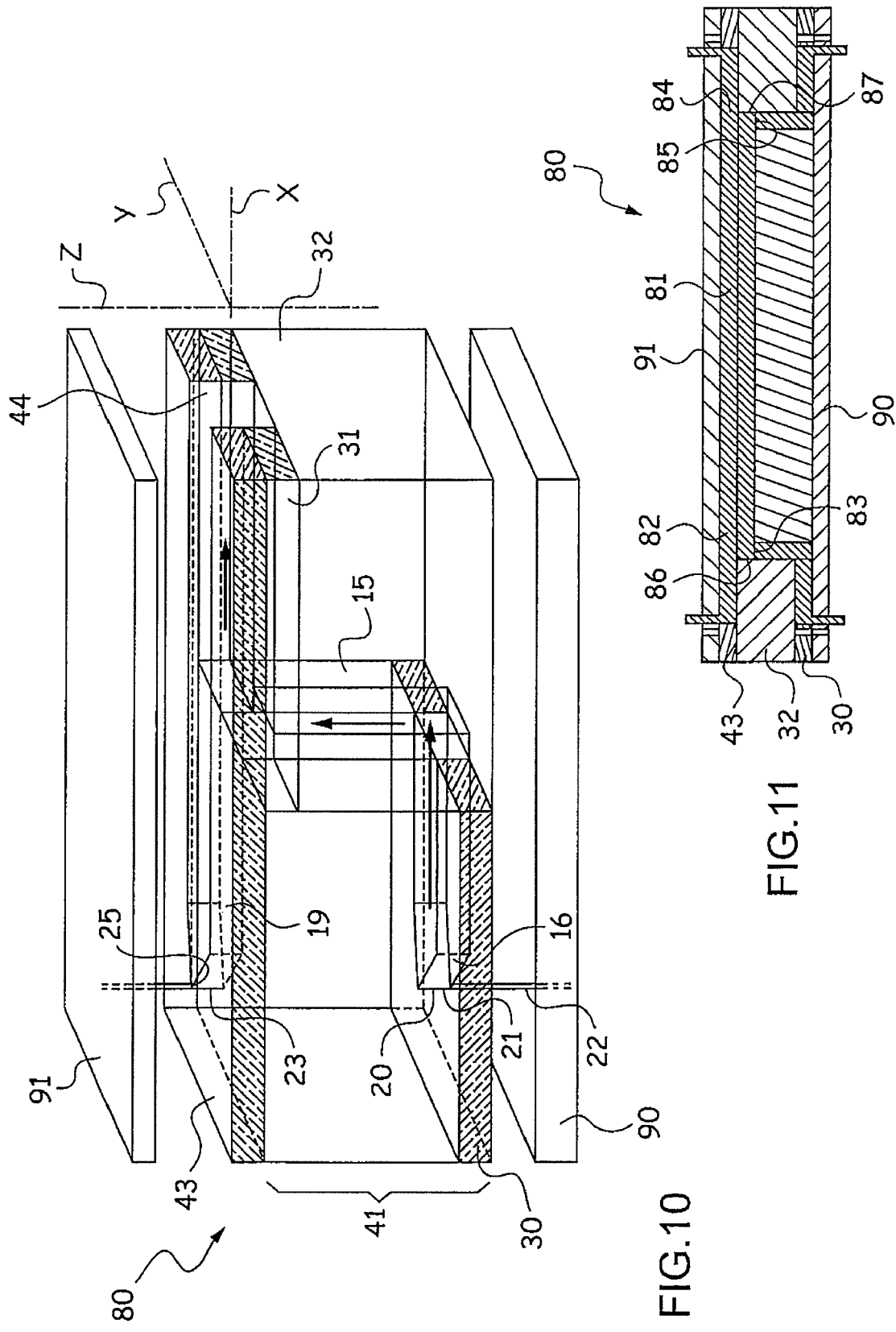
FIG. 10 is a diagrammatic and fragmentary perspective view showing different elements of a device constituting another embodiment of the invention.
FIG. 11 is a diagrammatic and fragmentary section view of the FIG. 10 device.

FIG. 11 shows a fluidic separator device 80 constituting another embodiment of the invention.

This device 80 has a microchannel 81 with first and second inlets 82 and 83 and first and second outlets 84 and 85.

The inlets 82 and 83 are separated by a transverse separation wall 86 and the outlets 84 and 85 are separated by a transverse separation wall 87.

As shown in FIG. 10, the device 80 is made up of an assembly 41 as described above, a sheet 43, and two plates 90 and 91, with the plate 90 pressing against the sheet 30 and the plate 32, and the plate against the sheet 43.

The plates 32, 90, and 91 are substantially rigid, and the sheets 30, 31, and 43 are substantially flexible.

The plates 32, 90, and 91 may be made out of plastics material, in particular, e.g. out of Plexiglass® or Altuglas®, or they may be based on silica or on glass.

The plate 32 may be made using the usual microfluidic techniques, e.g. by using PDMS, S8, or any other polymer material, or indeed by using silica masks, this list not being limiting.

The duct 15 may be made up of three pieces that are adhesively bonded together and configured to form a slot defining the duct 15.

In a variant, the duct 15 may be formed by a slot dug out in a piece of plastics material.

The outlets 84 and 85 are made in a manner analogous to the inlets 82 and 83.

The invention claimed is:

1. A fluidic separation device comprising:
   at least one microchannel extending along a longitudinal axis (X), the microchannel having a cross-section that presents a width measured along a first transverse axis (Y) and a thickness measured along a second transverse axis (Z) perpendicular to the first, the width being greater than the thickness, the microchannel including, along the second transverse axis, bottom and top walls;
   at least first, second, and third inlets in fluidic communication with the microchannel, the second inlet being disposed on the second transverse axis (Z) between the first and third inlets; and
   at least first and second transverse separation walls respectively separating the first and second inlets and the second and third inlets, the first and second separation walls being arranged in such a manner that the second inlet is separated from each of said bottom and top walls by a non-zero distance measured along the second transverse axis (Z), the second inlet being adjacent to at least one of the separation walls.

2. A device according to claim 1, wherein the width/thickness ratio of the microchannel is greater than 2.

3. A device according to claim 1, wherein the microchannel presents a cross-section that is substantially rectangular.

4. A device according to claim 1, wherein at least one of said three inlets presents a width that is not less than the width of the microchannel.

5. A device according to claim 1, wherein at least one of the three inlets opens out in one of the bottom and top walls of the microchannel, and another one of the three inlets opens out in the other one of the bottom and top walls of the microchannel.

6. A device according to claim 5, wherein the first and third inlets are placed facing each other.

7. A device according to claim 1, wherein said at least three inlets all open out either into the bottom wall or into the top wall of the microchannel.

8. A device according to claim 1, wherein the first and third inlets are offset relative to each other along the longitudinal axis of the microchannel.

9. A device according to claim 1, wherein the second inlet opens out into the microchannel parallel to its longitudinal axis (X).

10. A device according to claim 1, wherein the second inlet is adjacent to or upstream from at least one of the separation walls.

11. A device according to claim 1, including at least one feed orifice associated with one of said three inlets, the feed orifice being in fluidic communication with said inlet via a duct, the duct including a diverging portion that diverges from a tip of the duct, the feed orifice opening out into the duct adjacent to said tip, and perpendicularly to the duct.

12. A device according to claim 1, including at least first and second outlets in fluidic communication with the microchannel, and separated from each other by a transverse separation wall of non-zero height measured along the second transverse axis (Z).

13. A device according to claim 12, wherein the first and second outlets are offset from each other along the longitudinal axis of the microchannel.

14. A device according to claim 12, wherein the first and second outlets are disposed facing each other.

15. A device according to claim 12, further comprising a third outlet, the second outlet being disposed between the first and third outlets along the second transverse axis, the first and second outlets and the second and third outlets being mutually separated by respective transverse separation walls of non-zero height measured along the second transverse axis.

16. A device according to claim 12, including at least one outlet orifice associated with one of said outlets, said orifice being in fluidic communication with said outlets via a duct, the duct including a portion that converges towards a tip, the outlet orifice opening out into the duct perpendicularly to the duct.

17. A device according to claim 1, which is arranged to generate within at least a fraction of the microchannel at least one transverse force field, said force field selected from the group consisting of a gravitational, electric, magnetic, or acoustic field.

18. A device according to claim 1, including at least one sheet of plastics material or of metal forming the microchannel at least in part, the sheet being sandwiched between at least two plates of plastics material.

19. A device according to claim 1, including an array of parallel microchannels.

20. A fluidic separation device comprising:
   at least one microchannel extending along a longitudinal axis (X), the microchannel having a cross-section presenting a width measured along a first transverse axis (Y) and a thickness measured along a second transverse axis (Z) perpendicular to the first, the width being greater than the thickness, the microchannel including along the second transverse axis, bottom and top walls;
   at least first and second inlets in fluidic communication with the microchannel; and
   at least one transverse separation wall separating the first and second inlets, said separation wall being arranged in such a manner that the second inlet is separated from one of said bottom and top walls by a non-zero distance measured along the second transverse axis (Z), the second inlet being adjacent to the separation wall;
   the device including at least one sheet having a cutout forming at least part of a flow channel, said sheet being sandwiched between at least two plates.

* * * * *

UNITED STATES PATENT AND TRADEMARK OFFICE
CERTIFICATE OF CORRECTION

PATENT NO. : 7,897,044 B2  Page 1 of 1
APPLICATION NO. : 11/851711
DATED : March 1, 2011
INVENTOR(S) : Hoyos et al.

It is certified that error appears in the above-identified patent and that said Letters Patent is hereby corrected as shown below:

Title page,
Item (63) should read:
--Related U.S. Application Data
(63)  Continuation of application No. PCT/FR2006/050216, filed on March 13, 2006.--.

Signed and Sealed this
Third Day of April, 2012

David J. Kappos
*Director of the United States Patent and Trademark Office*